United States Patent [19]

Marcuse

[11] 4,181,433
[45] Jan. 1, 1980

[54] METHOD FOR DETERMINING THE REFRACTIVE INDEX PROFILE OF OPTICAL FIBERS AND OPTICAL FIBER PREFORMS

[75] Inventor: Dietrich Marcuse, Lincroft, N.J.

[73] Assignee: Bell Telephone Laboratories, Incorporated, Murray Hill, N.J.

[21] Appl. No.: 896,347

[22] Filed: Apr. 14, 1978

[51] Int. Cl.² .................. G01N 21/22; G01N 21/46
[52] U.S. Cl. ................................... 356/73.1; 356/128
[58] Field of Search ................. 356/73.1, 125, 128, 356/124

[56] References Cited

PUBLICATIONS

Brinkmeyer, E., "Refractive-Index Profile Determination of Optical Fibers by Spatial Filtering", Applied Optics, vol. 17, No. 1, 1 Jan. 1978.
Brinkmeyer, E., "Refractive-Index Profile Determination of Optical Fibers from the Diffraction Pattern", Applied Optics, vol. 16, No. 11, Nov. 1977.
Okoshi, et al. "Refractive-Index Profile of an Optical Fiber: Its Measurement by the Scattering-Pattern Method", Applied Optics, vol. 15, No. 11, Nov. 1976.

*Primary Examiner*—John K. Corbin
*Assistant Examiner*—Bruce Y. Arnold
*Attorney, Agent, or Firm*—Sylvan Sherman

[57] ABSTRACT

This application describes a nondestructive method for determining the refractive index profile of optical fibers and fiber preforms by measuring the density distribution of the light that is focused by the fiber/preform core acting as the lens. The fiber/preform is immersed in an index matching medium and illuminated by means of a collimated light beam directed at right angles to the fiber/preform axis. The density distribution of the light focused by the fiber/preform core is then measured along a direction normal to the fiber/preform axis at a distance L from the axis that is less than the focal length of the fiber/preform. The index profile is determined from these measurements by two numerical integrations.

3 Claims, 2 Drawing Figures

METHOD FOR DETERMINING THE REFRACTIVE INDEX PROFILE OF OPTICAL FIBERS AND OPTICAL FIBER PREFORMS

TECHNICAL FIELD

This invention relates to a method for determining the refractive index profile of optical fibers and optical fiber preforms.

BACKGROUND OF THE INVENTION

In U.S. Pat. No. 3,434,774, it is disclosed that more efficient transmission of optical wave energy along a multimode optical fiber is achieved by grading the refractive index of the fiber core. However, the degree of efficiency that can be derived is determined by how closely the fiber's refractive index profile approaches the optimum distribution. Thus, an accurate knowledge of the profile is necessary in order to assess the fiber's transmission properties.

At present, the most sensitive technique used to obtain fiber profile information is interference microscopy. In application, a very thin transverse sample of the fiber to be tested is prepared and, when placed in one branch of an interferometer, serves as a phase object. Because of its graded-index, the phase shift produced by the core region of the fiber sample is not uniform, resulting in a displacement in the fringe pattern produced by the interferometer. The fringe displacement, or shift, at any point, is proportional to the index difference, $\Delta n$, between the cladding index, which is typically uniform, and the core index at that point. Thus, to obtain the index distribution over the area of the core, the fringe displacement must be carefully measured at a large number of points consistent with the degree of accuracy desired.

The principal problem with this technique is that it is destructive in that a sample of the fiber must be taken. In addition, a very time consuming preparation of the sample is required.

The distribution of the refractive index in the core of a fiber or preform can also be determined by observing the light trajectories of individual rays as they traverse the core, as described by P. L. Chu in an article entitled "Nondestructive Measurement of Index Profile of an Optical-Fiber Preform," Electr. Letters, Nov. 24, 1977, Vol. 13, No. 24, pp. 736–738. The problem with this technique is that it requires the use of very thin pencils of light, and very careful measurements of ray angles.

SUMMARY OF THE INVENTION

In accordance with the present invention the refractive index profile of a fiber or fiber preform is obtained by measuring the power density distribution of a light field focused by the fiber/preform core region. The refractive index distribution is obtained by performing two numerical integrations. The first integration establishes the relationship between the output and input ray positions from the observed power distribution. The second integration determines the index profile. Thus, the method comprises the steps of immersing the fiber/preform in an index matching medium; illuminating the fiber/preform along a direction perpendicular to its axis; and measuring, along a direction transverse to the fiber/preform axis, the intensity distribution of the light focused by the fiber/preform; characterized in that said measurements are made at a distance from the fiber/preform that is less than its focal length; and by the further step of determining, from said measurements, the refractive index profile of the fiber/preform.

It is an advantage of the invention that both fibers and preforms can be measured. It is a further advantage that the measurement is nondestructive of either fiber or preform, and no preparation of samples is required. In addition, the profile can be measured at any position along the length of a fiber or preform and is not restricted to any particular sample. Finally, the entire process can be automated and results obtained within a matter of minutes.

DETAILED DESCRIPTION

Figure 1:
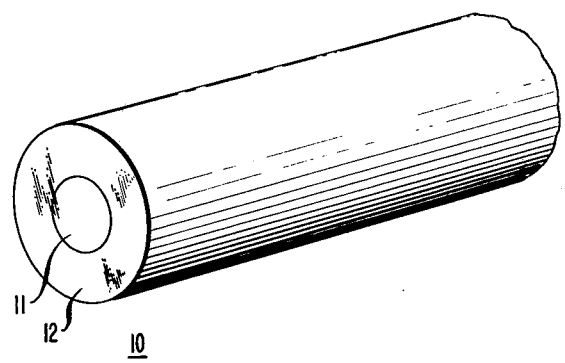
FIG. 1 shows a portion of a fiber/preform to which the invention relates.

Referring to the drawings, FIG. 1 shows a portion of an optical fiber 10 comprising an inner core region 11 surrounded by a cladding 12. FIG. 1 is equally representative of a fiber preform and, insofar as the present invention is concerned, all references to an optical fiber are equally applicable to fiber preforms and, for this reasons, the term "fiber/preform" is used hereinafter.

Figure 2:
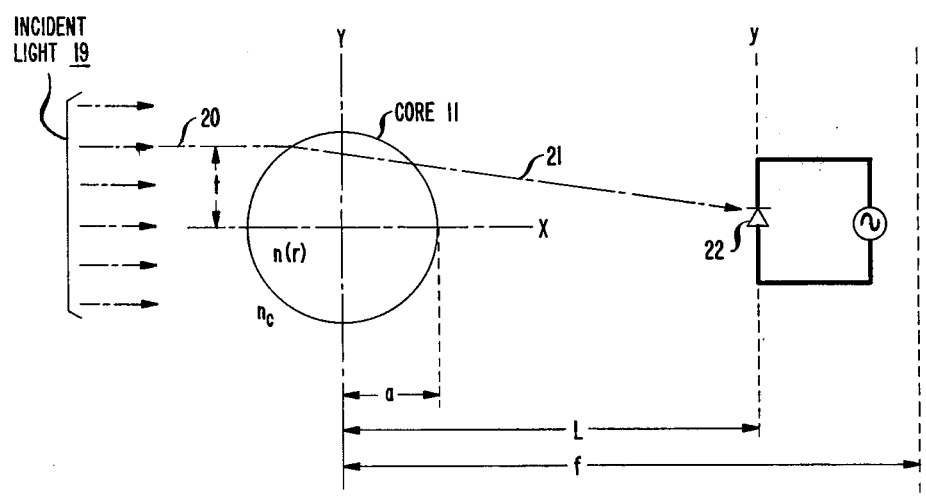
FIG. 2 shows an arrangement for determining the index profile of a fiber/preform in accordance with the present invention.

Typically, in a multimode optical fiber, the refractive index of the core is graded, being a maximum at the center of the fiber and decreasing to some minimum value at the core-cladding interface. The grading is for the purpose of minimizing mode dispersion and, as noted hereinabove, the degree to which this is accomplished depends upon how closely the grading follows the optimum profile for the particular materials used in the fabrication of the fiber. Accordingly, it is important to be able to ascertain the index profile of a fiber or, preferably, to be able to determine the index profile of the fiber preform before the fiber is drawn. This is done, in accordance with the present invention, by immersing the fiber/preform in an index-matching liquid, and illuminating it by means of a beam of coherent or incoherent light directed at right angles to the fiber/preform axis. FIG. 2 shows the incident light 19 and, in particular, one input ray 20 as it enters the core 11 of the fiber/preform, and the corresponding refracted output ray 21. Photooptic means 22, located at a distance L from the fiber/preform center, measures the light intensity along the Y direction orthogonal to the fiber/preform axis. If the fiber/preform core, acting as a lens, has a focal length f, the distance L along which measurements are made, is selected to be less than f.

With the photooptic means located within the index-matching medium, the expression for the refractive index profile n(r) is given by $$n(r) = \frac{n_c}{\pi L} \int_r^a \frac{t - y(t)}{\sqrt{t^2 - r^2}} \, dt + n_c \quad (1)$$

where $n_c$ is the refractive index of the fiber/preform cladding;

a is the radius of the fiber/preform core y(t) is a function that defines the position of an output ray at the measuring plane as a function of the position (t) of the corresponding input ray.

The function y(t) is obtained from the intensity measurements by first obtain the inverse relationship t(y) given by $$t(y) = \int_0^y P(y')dy'; \quad (2)$$

where $P(y')$ is the measured light intensity at points $y'$ along the measuring plane.

Having determined t(y) from equation (2), the inverse function y(t) is readily obtained and then used in the solution of equation (1).

If the light is permitted to leave the index matching medium before entering into the photooptical measuring device, Snell's law must be taken into account. The result is to modify equation (1) to read $$n(r) = \frac{1}{\pi L} \int_r^a \frac{t - y(t)}{\sqrt{t^2 - r^2}} dt + n_c \quad (3)$$

SUMMARY

A method for determining the refractive index profile of optical fibers and preforms is disclosed by employing a beam of collimated light incident at right angles to the core axis. The refractive index distribution is obtained from an evalution of the power distribution of the light focussed by the core. While the distance between the fiber/peform and the measuring plane is not at all critical, it should not be close to the paraxial focal point of the core.

The procedure for determining the index distribution is as follows: (a) measure the power density distribution of the light field at a convenient distance from the fiber/preform; (b) normalize the measured values so the $P(y)$ has a value of unity for $y \geq a$; (c) the function $P(y)$ is substituted into equation (2) and the function t(y) obtained by numerical integration; (d) function t(y) is inverted by sorting out the t-y number pairs; (e) the function y(t) is then substituted in either equation (1) or (3) to obtain n(r) by numerical integration.

The method requires relatively simple equipment for its instrumentation. A source of collimated incoherent light provides the incident illumination. For the observation of preforms, a single diode detector can be moved to measure the power density. An array of scanning diode detectors or a videcon can be used for increased speed of data acquisition. For measuring fibers, a microscope is used to magnify the image in the observation plane for scanning purposes. However, a relatively inexpensive microscope is sufficient for this purpose. If desired, the entire process can be automated using the equipment described in the copending application Ser. No. 890,869 filed Mar. 28, 1978 and assigned to applicants' assignee.

I claim:

1. A method for determining the refractive index profile of an optical fiber and an optical fiber preform comprising the steps of:
    immersing said fiber/preform in an index matching medium;
    illuminating said fiber/preform;
    measuring, along a direction transverse to the longitudinal axis of said fiber/preform, the intensity distribution of radiant energy focused by said fiber/preform;
CHARACTERIZED IN THAT
said measurement is made at a distance from the center of said fiber/preform that is less than the focal length of said fiber/preform;
and by the further step of determining from said measurement the refractive index profile of said fiber/preform.

2. The method according to claim 1
CHARACTERIZED IN THAT:
the index profile n(r) is given by $$n(r) = \frac{n_c}{\pi L} \int_r^a \frac{t - y(t)}{\sqrt{t^2 - r^2}} dt + n_c;$$

where
$n_c$ is the refractive index of the fiber/preform cladding;
a is the radius of the fiber/preform core; L is the distance from the fiber/preform core center at which the measurements are made;
r is the radial distance from the center of the fiber-preform core; and
y(t) is the function that defines the position of an output ray at the measuring plane as a function of the position (t) of the corresponding input ray, and is the inverse of the function t(y) given by $$t(y) = \int_0^y P(y')dy';$$

$P(y')$ is the measured light intensity along the measuring plane; and the output light is confined within the index matching medium.

3. The method according to claim 1
CHARACTERIZED IN THAT
the index profile n(r) is given by $$n(r) = \frac{1}{\pi L} \int_r^a \frac{t - y(t)}{t^2 - r^2} dt + n_c;$$

where
$n_c$ is the refractive index of the fiber/preform cladding;
a is the radius of the fiber/preform core; L is the distnace from the fiber/preform core center at which the measurements are made;
r is the radial distance from the center of the fiber-preform core; and
y(t) is the function that defines the position of an output ray at the measuring plane as a function of the position (t) of the corresponding input ray and is the inverse of the function t(y) given by $$t(y) = \int_0^y P(y')dy';$$

where
$P(y')$ is the measured light intensity along the measuring plane;
and the output light leaves the index matching medium before entering the measuring means.

* * * * *